United States Patent
Linz et al.

(10) Patent No.: US 7,169,934 B2
(45) Date of Patent: Jan. 30, 2007

(54) (R) 2-(4-AMIDINOPHENYLAMINO-METHYL)-1-METHYL-5-[1-(CARBOXYMETHYLAMINO)-1 (PYRROLIDINOCARBONYL)-ETHYL]-BENZIMIDAZOLE, THE MONOHYDROCHLORIDE THEREOF, PREPARATION THEREOF AND THE USE AS PHARMACEUTICAL COMPOSITION

(75) Inventors: Guenter Linz, Mittelbiberach (DE); Peter Sieger, Mittelbiberach (DE); Gunnar Schreiner, Biberach (DE); Werner Rall, Mittelbiberach (DE); Rolf Schmid, Baltringen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 201 days.

(21) Appl. No.: 10/463,033

(22) Filed: Jun. 17, 2003

(65) Prior Publication Data

US 2004/0010026 A1    Jan. 15, 2004

Related U.S. Application Data

(60) Provisional application No. 60/395,188, filed on Jul. 11, 2002.

(30) Foreign Application Priority Data

Jun. 20, 2002 (DE) ............... 102 27 666

(51) Int. Cl.
  *C07D 403/06* (2006.01)
(52) U.S. Cl. .................. 548/306.1
(58) Field of Classification Search ............ 548/306.1; 514/394

See application file for complete search history.

(56) References Cited

U.S. PATENT DOCUMENTS 6,451,832 B2 *  9/2002  Ries et al. ............ 514/394
2003/0004356 A1  1/2003  Ries et al.

FOREIGN PATENT DOCUMENTS

WO    WO 00/01704    *   1/2000

* cited by examiner

*Primary Examiner*—Joseph K. McKane
*Assistant Examiner*—Andrew B. Freistein
(74) *Attorney, Agent, or Firm*—Alan Stempel; Mary-Ellen Devlin; Michael Morris

(57) ABSTRACT

Crystalline forms of the compounds (R)-2-(4-amidinophenylaminomethyl)-1-methyl-5-[1-(carboxymethylamino)-1-(pyrrolidinocarbonyl)-ethyl]-benzimidazole and the monohydrochloride thereof, processes for the preparation thereof and the use thereof as pharmaceutical compositions.

2 Claims, 2 Drawing Sheets

Figure 1: X-ray powder diffractogram of the compound (R)-2-(4-amidinophenyl-aminomethyl)-1-methyl-5-[1-(carboxymethylamino)-1-(pyrrolidinocarbonyl)-ethyl]-benzimidazole-monohydrochloride
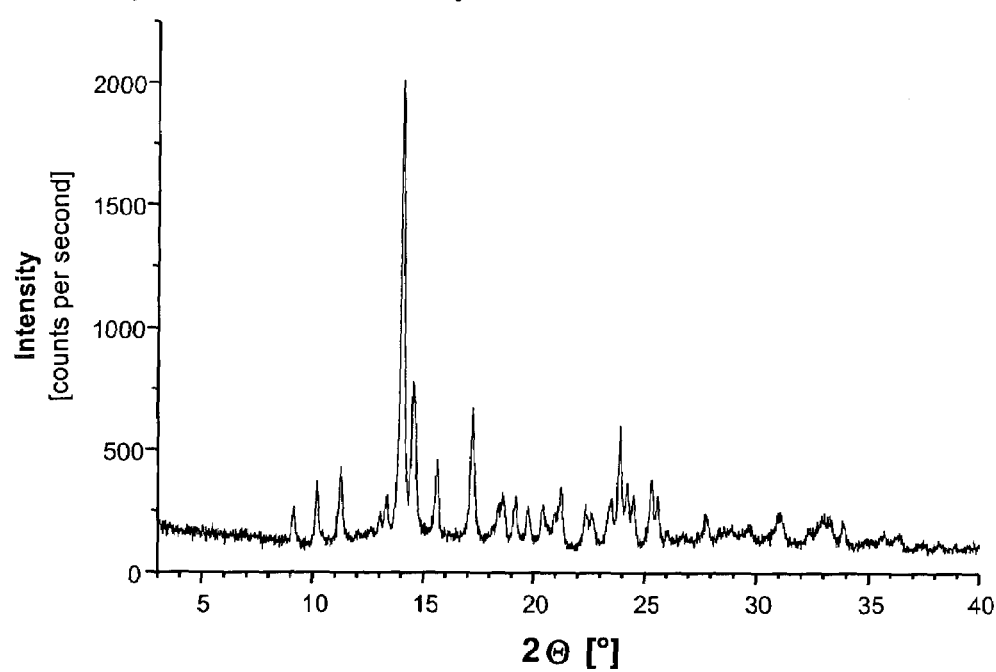

Figure 2: X-ray powder diffractogram of the compound (R)-2-(4-amidinophenyl-aminomethyl)-1-methyl-5-[1-(carboxymethylamino)-1-(pyrrolidinocarbonyl)-ethyl]-benzimidazole
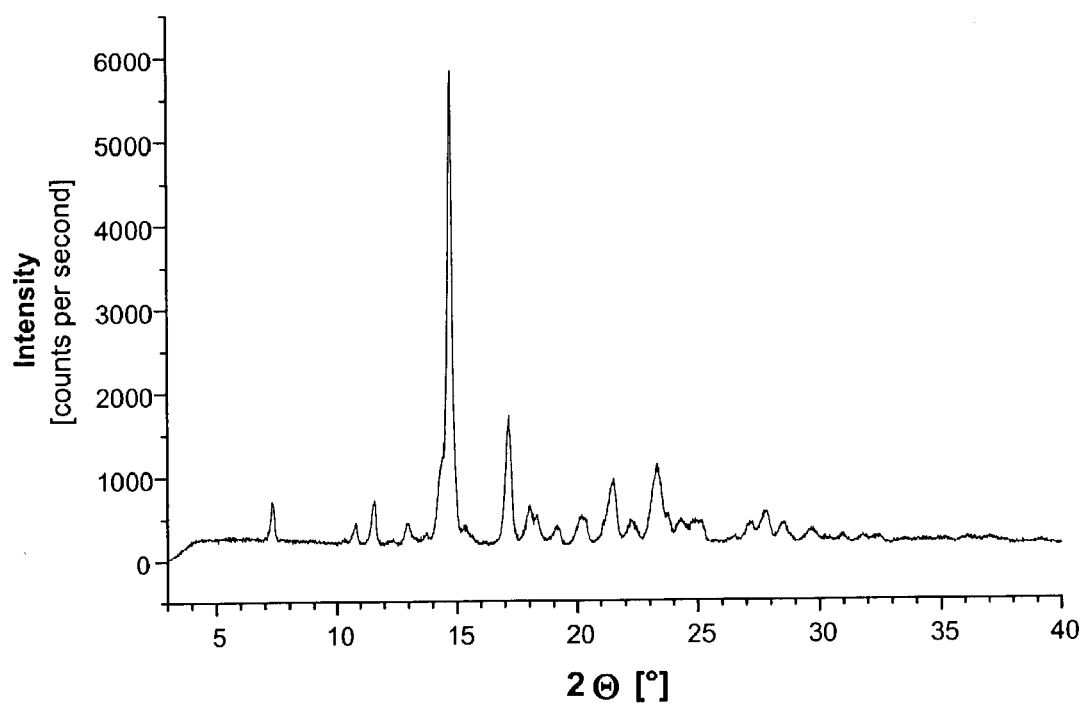

(R) 2-(4-AMIDINOPHENYLAMINO-METHYL)-1-METHYL-5-[1-(CARBOXY-METHYLAMINO)-1 (PYRROLIDINOCARBONYL)-ETHYL]-BENZIMIDAZOLE, THE MONOHYDROCHLORIDE THEREOF, PREPARATION THEREOF AND THE USE AS PHARMACEUTICAL COMPOSITION

RELATED APPLICATIONS

Benefit of U.S. Provisional Application Ser. No. 60/395,188, filed on Jul. 11, 2002 is hereby claimed.

FIELD OF THE INVENTION

The present invention relates to the crystalline forms of the compounds (R)-2-(4-amidinophenylaminomethyl)-1-methyl-5-[1-(carboxymethylamino)-1-(pyrrolidinocarbonyl)-ethyl]-benzimidazole and the monohydrochloride thereof, processes for the preparation thereof and the use thereof as pharmaceutical compositions.

BACKGROUND TO THE INVENTION

A number of benzimidazole derivatives are known in the prior art. Thus, for example, International Patent Application WO 00/01704 discloses benzimidazole derivatives which have valuable pharmacological properties, particularly an antithrombotic activity, which is based, for example, on a thrombin-inhibiting or factor Xa-inhibiting activity.

By virtue of their pharmacological properties, the compounds (R)-2-(4-amidinophenyl-aminomethyl)-1-methyl-5-[1-(carboxymethylamino)-1-(pyrrolidinocarbonyl)-ethyl]-benzimidazole and the monohydrochloride thereof may be used for the prevention and treatment of venous thromboses in various vascular areas, including deep and superficial leg vein thromboses, vena cava thromboses, thromboses of the renal and hepatic veins including veno-occlusive disease, for the prevention and treatment of pulmonary embolism, for the treatment of patients with all forms of coronary heart disease, including the acute form, as unstable angina pectoris or acute myocardial infarct, and the chronic form, as stable angina pectoris, or in patients with post-myocardial infarct condition, for preventing acute and chronic reocclusions after bypass operations on all vascular areas and after angioplasty (PT(C)A), and for preventing occlusion in patients with peripheral arterial diseases, for treating stroke in its acute form, in the chronic form in patients with post-stroke conditions and for primary prophylaxis in patients with stenoses of the afferent cerebral arteries.

The benzimidazoles mentioned above may also be used to treat patients on kidney replacement therapy. This comprises both anticoagulation during the use of kidney replacement therapy to keep the system open and also treatment of the system activation of clotting such as occurs in patients on kidney replacement therapy, both in patients undergoing chronic haemodialysis and in those undergoing a process of veno-venous or arterio-venous chronic filtration. Accordingly, both patients with chronic kidney failure and patients with acute kidney failure may be treated irrespective of the cause of the kidney failure. This also includes the prevention and treatment of blockage of the dialysis shunt.

The abovementioned pharmacologically valuable properties of the benzimidazole derivatives disclosed in the prior art constitute the basic prerequisite for effective use of the compounds as pharmaceutical compositions. However, to be permitted for use as a medicament, an active substance must also satisfy further requirements. These parameters are largely to do with the physicochemical nature of the active substance.

Without being restrictive, examples of these parameters are the stability of effect of the starting substance under various environmental conditions, the stability during production of the pharmaceutical formulation and stability in the final compositions of the drug. The pharmaceutically active substance used to prepare the pharmaceutical compositions should therefore have great stability which is ensured even under all kinds of environmental conditions. This is absolutely essential to prevent pharmaceutical compositions being used which contain breakdown products, for example, in addition to the active substance itself. In such a case the content of active substance present in the pharmaceutical formulation might be lower than specified.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, a pharmaceutically active substance should be only slightly hygroscopic.

As the crystal modification of an active substance is important to the reproducible active substance content of a preparation, there is a need to clarify as far as possible any existing polymorphism of an active substance present in crystalline form. If there are different polymorphism modifications of an active substance care must be taken to ensure that the crystalline modification of the substance does not change in the pharmaceutical preparation later produced from it. Otherwise, this could have a harmful effect on the reproducible potency of the drug. Against this background, active substances characterised by only slight polymorphism are preferred.

Another criterion which may be of exceptional importance under certain circumstances depending on the choice of formulation or the choice of manufacturing process is the solubility of the active substance. If for example pharmaceutical solutions are prepared (e.g. for infusions) it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicochemical requirements as far as possible.

DETAILED DESCRIPTION OF THE INVENTION

Surprisingly, it has been found that the problem outlined above is solved by the crystalline monohydrochloride of the compound (R)-2-(4-amidinophenylaminomethyl)-1-methyl-5-[1-(carboxymethylamino)-1-(pyrrolidinocarbonyl)-ethyl]-benzimidazole of formula (I):

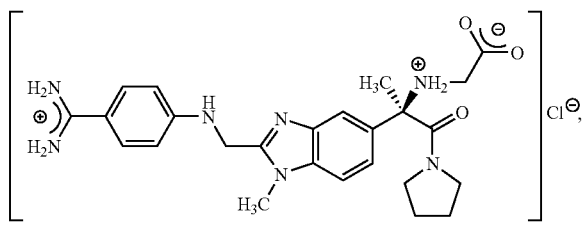

The monohydrochloride according to the invention is characterised by a high degree of stability and dissolves very easily in physiologically acceptable solvents.

The crystalline form of the monohydrochloride of the compound (R)-2-(4-amidinophenylaminomethyl)-1-methyl-5-[1-(carboxymethylamino)-1-(pyrrolidinocarbonyl)-ethyl] according to the invention is characterised by a melting point of $T_{m.p.}=222°$ C.±5° C. (determined by DSC=Differential Scanning Calorimetry; evaluated by the onset; heating rate: 10° C./min). The value given was determined using a DSC 821 made by Messrs Mettler Toledo.

Therefore a first object of the present invention is the crystalline monohydrochloride of the compound (R)-2-(4-amidinophenylaminomethyl)-1-methyl-5-[1-(carboxymethylamino)-1-(pyrrolidinocarbonyl)-ethyl]-benzimidazole, characterised by a melting point of $T_{m.p.}=222°$ C.±5° C.

The crystalline form of the (R)-2-(4-amidinophenylaminomethyl)-1-methyl-5-[1-(carboxymethylamino)-1-(pyrrolidinocarbonyl )-ethyl]-benzimidazole monohydrochloride according to the invention was examined more closely by X-ray powder diffraction. The diagram obtained is shown in FIG. 1.

Table 1 that follows summarises the data obtained in this analysis:

TABLE 1

X-ray powder reflections and intensities (standardised) of (R)-2-(4-amidinophenylaminomethyl)-1-methyl-5-[1-(carboxymethylamino)-1-(pyrrolidinocarbonyl-ethyl]-benzimidazole-monohydrochloride.

| 2 Θ [°] | $d_{hkl}$ [Å] | intensity $I/I_o$ [%] | 2 Θ [°] | $d_{hkl}$ [Å] | intensity $I/I_o$ [%] |
|---|---|---|---|---|---|
| 9.17 | 9.64 | 13 | 22.66 | 3.92 | 12 |
| 10.21 | 8.66 | 19 | 23.50 | 3.78 | 15 |
| 11.28 | 7.84 | 21 | 23.90 | 3.72 | 30 |
| 13.06 | 6.77 | 11 | 24.22 | 3.67 | 18 |
| 13.34 | 6.63 | 16 | 24.51 | 3.63 | 16 |
| 14.03 | 6.31 | 100 | 25.33 | 3.51 | 19 |
| 14.57 | 6.07 | 38 | 25.63 | 3.47 | 16 |
| 15.62 | 5.67 | 23 | 26.04 | 3.42 | 9 |
| 17.22 | 5.14 | 34 | 27.83 | 3.20 | 12 |
| 18.45 | 4.80 | 14 | 29.76 | 3.00 | 10 |
| 18.63 | 4.76 | 16 | 31.10 | 2.87 | 12 |
| 19.19 | 4.62 | 16 | 32.39 | 2.76 | 8 |
| 19.78 | 4.48 | 13 | 32.98 | 2.71 | 11 |
| 20.45 | 4.34 | 14 | 33.32 | 2.69 | 12 |
| 20.99 | 4.23 | 12 | 33.89 | 2.64 | 10 |
| 21.24 | 4.18 | 17 | 35.73 | 2.51 | 9 |
| 22.39 | 3.97 | 14 | 36.34 | 2.47 | 8 |

In Table 1 above the value "2Θ[°]" denotes the angle of diffraction in degrees and the value "$d_{hkl}$[Å]" denotes the specified distances in Å between the lattice planes.

The x-ray powder diagram was recorded, within the scope of the present invention, using a Bruker D8 Advanced Diffractometer fitted with a location-sensitive detector (OED) and a Cu anode as the x-ray source (CuK$_\alpha$ radiation, λ=1.5418 Å, 30 kV, 40 mA).

According to the findings shown in Table 1 the present invention relates to crystalline (R)-2-(4-amidinophenylaminomethyl)-1-methyl-5-[1-(carboxymethylamino)-1-(pyrrolidinocarbonyl)-ethyl]-benzimidazole-monohydrochloride, characterised in that in the x-ray powder diagram it has, inter alia, the characteristic values d=6.31 Å, 6.07 Å, 5.14 Å and 3.72 Å.

The crystalline monohydrochloride of the compound (R)-2-(4-amidinophenylaminomethyl)-1-methyl-5-[1-(carboxymethylamino)-1-(pyrrolidinocarbonyl)-ethyl]-benzimidazole according to the invention occurs in the form of hydrates which, depending on the relative humidity, contain between about 3.0% and 6.5% water. By virtue of its structure the compound is capable of absorbing water of crystallisation and releasing it again without the crystalline structure changing fundamentally.

Moreover, the monohydrochloride according to the invention forms solvates with organic solvents, e.g. with ethanol.

A second object of the present invention is a process for preparing the crystalline salt (R)-2-(4-amidinophenylaminomethyl)-1-methyl-5-[1-(carboxymethylamino)-1-(pyrrolidinocarbonyl)-ethyl]-benzimidazole-monohydrochloride according to the invention, comprising the following steps:

Step (a):

The starting material used is the (R)-2-(4-cyanophenylaminomethyl)-1-methyl-5-[1-amino-1-(pyrrolidinocarbonyl)-ethyl]-benzimidazole of formula (II) already described in WO 00/01704:

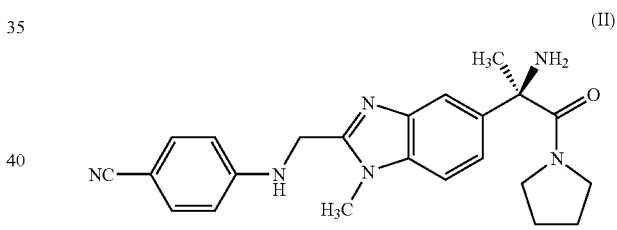

The free primary amino group is alkylated for example with 1 to 1.5 equivalents, preferably with about 1.2 equivalents, of a compound of general formula

wherein R denotes a $C_{1-3}$-alkyl group and X denotes a leaving group, for example a halogen atom such as the chlorine, bromine or iodine atom, the p-toluenesulphonyl or methanesulphonyl group, of which ethyl bromoacetate or n-propyl bromoacetate is preferably used, in an organic solvent or mixture of solvents, in the presence of a base. Suitable solvents according to the invention include ethyl acetate, n-propyl acetate, N-methylpyrrolidinone, dimethylformamide, dimethylacetamide or mixtures thereof. According to the invention, a solvent mixture consisting of N-methylpyrrolidinone and ethyl acetate or n-propyl acetate is used. Suitable bases include for example tertiary amines such as diisopropylethylamine (Hünig base) or triethylamine in an amount of 1 to 2.5 equivalents. The reaction is preferably carried out at temperatures between 0° C. and the boiling temperature of the solvent mixture, e.g. between 0° C. and 150° C., preferably between 10° C. and 30° C.

Purification of the reaction mixture through aqueous extractions yields, after partial evaporation of the organic solvent, a concentrated solution of crude (R)-2-(4-cyanophenylaminomethyl)-1-methyl-5-[1-(n-$C_{1-3}$-alkyloxycarbonylmethylamino)-1-(pyrrolidinocarbonyl)-ethyl]-benzimidazole of general formula

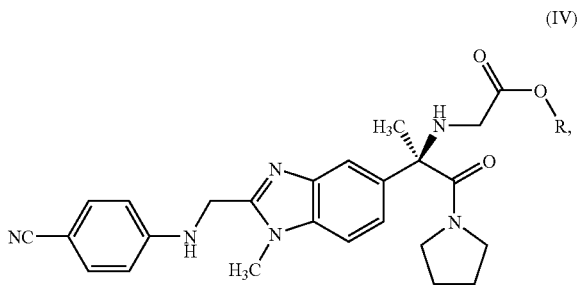

(IV)

wherein R denotes a $C_{1-3}$-alkyl group.

Step (b):

The concentrated solution of the crude compound of formula (IV) obtained in step (b) is dissolved in a $C_{1-3}$-alcohol as solvent and reacted by piping in hydrogen chloride gas, with cooling, preferably at a temperature below about 20° C., to produce the imino ester as intermediate. According to the invention methanol, ethanol or n-propanol is preferably used as alcohol, while the choice of solvent depends on the ester of formula (IV) used. Once all the hydrogen chloride gas has been piped in the reaction mixture is stirred until the reaction is complete at a temperature between 0° C. and 30° C., preferably at about 20° C.

The conversion of the iminoester into an amidine of general formula

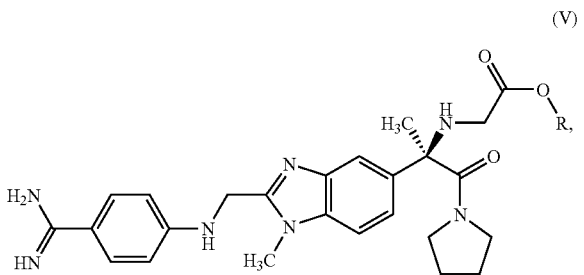

(V)

wherein R denotes a $C_{1-3}$-alkyl group, is carried out with cooling, preferably at temperatures between 0° C. and 40° C., most preferably at 15° C. to 40° C., by reacting with an aqueous ammonia solution in a $C_{1-3}$-alcohol, preferably methanol, ethanol or n-propanol. Once the reaction has ended, to obtain the amidine, ammonium chloride may be filtered off optionally after partial distillation of the solvent. The compound (V) may be intermediately isolated in the form of the hydrochloride or directly as the p-toluenesulphonic acid salts of general formula (VI) (cf. step c).

Step (c):

The intermediate compounds (R)-2-(4-amidinophenylaminomethyl)-1-methyl-5-[1-(n-$C_{1-3}$-alkyloxycarbonylmethylamino)-1-(pyrrolidinocarbonyl)-ethyl]-benzimidazole of general formula (V) are precipitated according to the invention in the form of sulphonic acid salts, for example in the form of benzene-, p-toluene-, p-chlorobenzene-, 1- or 2-naphthenesulphonic acid salts, most preferably in the form of the the p-toluenesulphonic acid salts of general formula (VI)

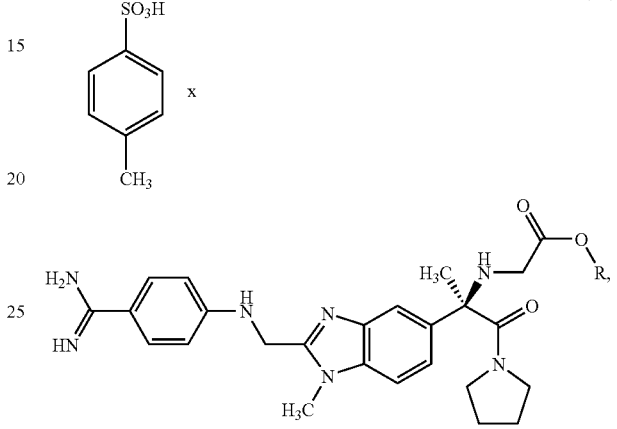

(VI)

wherein R denotes a $C_{1-3}$-alkyl group, enabling the compound to be easily isolated from the aqueous medium.

Further purification of the p-toluenesulphonic acid salts of the compounds of general formula (VI) is carried out by pH-controlled dissolving and precipitation of the salt in aqueous medium or by suspending in water.

Step (d):

In order to prepare the free base (R)-2-(4-amidinophenylaminomethyl)-1-methyl-5-[1-(carboxymethylamino)-1-(pyrrolidinocarbonyl)-ethyl]-benzimidazole of formula

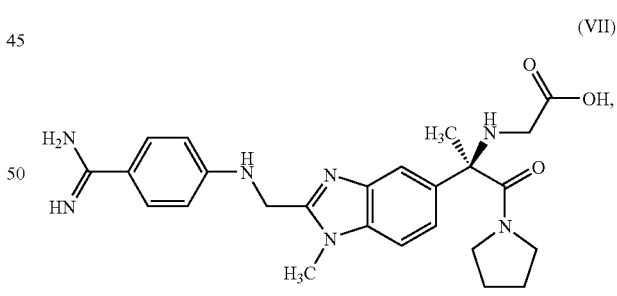

(VII)

the corresponding p-toluenesulphonic acid salt of general formula (VI) is dissolved in a suitable organic solvent. Suitable solvents include for example alcohols such as methanol, ethanol, i-propanol or polar solvents such as N-methylpyrrolidinone or dimethylformamide, preferably methanol or ethanol.

Then 1.5 to 3 equivalents, preferably 2 to 2.5 equivalents of a suitable base are added to this solution. Suitable bases within the scope of the present invention include sodium hydroxide, potassium hydroxide, lithium hydroxide and barium hydroxide. The reaction mixture can then be heated and in this way the progress of the reaction can be speeded up. Preferably, the reaction mixture is heated, with thorough mixing, to a temperature above 30° C., the maximum temperature which can be selected depending on the boiling temperature of the solvent used, preferably at temperatures between 30° C. and 80° C.

Then 0.5 to 2 equivalents, preferably 1 to 1.5 equivalents, of an acid, preferably p-toluenesulphonic acid, are added.

If sodium hydroxide is used as the base, the desired product of formula (VII) is obtained directly on crystallisation. If potassium hydroxide is used as base, the potassium salt of p-toluenesulphonic acid crystallises out first. Then the desired product of formula (VII) can be crystallised.

Step (e):

In order to prepare the crystalline monohydrochloride of general formula (I) according to the invention the base (VII) obtained in step (d) is suspended or dissolved in a suitable organic solvent or mixture of solvents. Particularly preferred solvents according to the invention include methanol, ethanol, n-propanol, i-propanol, acetone, dimethylformamide or N-methylpyrrolidinone. A certain amount of water may be added as cosolvent.

Then the reaction mixture is heated to a temperature between 20° C. and the reflux temperature of the solvent, preferably between 30° C. and 80° C. According to the invention, hydrogen chloride dissolved in an organic solvent or hydrochloric acid is added to the solution or suspension.

According to the invention 0.8 to 1.2 mol, preferably about 1 mol, of hydrogen chloride are added per mol of base used. After the acid has been added the suspension is cooled to a temperature between 0° C. and 40° C., preferably between 20° C. and 25° C. and the product is filtered off.

A third object of the invention relates to crystalline (R)-2-(4-amidinophenylaminomethyl)-1-methyl-5-[1-(carboxymethylamino)-1-(pyrrolidinocarbonyl)-ethyl]-benzimidazole-monohydrochloride, obtainable by the process described hereinbefore.

A fourth object of the invention is the use of the crystalline monohydrochloride of the compound (R)-2-(4-amidinophenylaminomethyl)-1-methyl-5-[1-(carboxymethylamino)-1-(pyrrolidinocarbonyl)-ethyl]-benzimidazole according to the invention as a pharmaceutical composition on account of its pharmaceutical activity.

The p-toluenesulphonic acid salts of general formula (VI) obtained as intermediates in the process described above are valuable intermediate products for preparing the crystalline (R)-2-(4-amidinophenylaminomethyl)-1-methyl-5-[1-(carboxymethylamino)-1-(pyrrolidinocarbonyl)-ethyl]-benzimidazole-monohydrochloride of formula (I).

A fifth object of the present invention thus consists of the p-toluenesulphonic acid salts of general formula (VI):
(1) (R)-2-(4-amidinophenylaminomethyl)-1-methyl-5-[1-(methyloxycarbonylmethylamino)-1-(pyrrolidinocarbonyl)-ethyl]-benzimidazole-p-toluenesulphonate,
(2) (R)-2-(4-amidinophenylaminomethyl)-1-methyl-5-[1-(ethyloxycarbonylmethylamino)-1-(pyrrolidinocarbonyl)-ethyl]-benzimidazole-p-toluenesulphonate and
(3) (R)-2-(4-amidinophenylaminomethyl)-1-methyl-5-[1-(n-propyloxycarbonylmethylamino)-1-(pyrrolidinocarbonyl)-ethyl]-benzimidazole-p-toluenesulphonate.

The crystalline form of the free base (R)-2-(4-amidinophenylaminomethyl)-1-methyl-5-[1-(carboxymethylamino)-1-(pyrrolidinocarbonyl)-ethyl]-benzimidazole is the direct precursor for preparing the monohydrochloride of formula (I) and also has the pharmacological activity described hereinbefore.

A sixth object of the present invention is therefore the crystalline form of the free base (R)-2-(4-amidinophenylaminomethyl)-1-methyl-5-[1-(carboxymethylamino)-1-(pyrrolidinocarbonyl)-ethyl]-benzimidazole, characterised by a melting point $T_{m.p.}$=241° C. ±5° C. (determined by DSC=Differential Scanning Calorimetry; evaluated by the onset; heating rate: 10° C. /min). The value givent was determined using a DSC 821 made by Messrs Mettler Toledo.

The crystalline form of the free base (R)-2-(4-amidinophenylaminomethyl)-1-methyl-5-[1-(carboxymethylamino)-1-(pyrrolidinocarbonyl)-ethyl]-benzimidazole according to the invention was investigated in more detail by x-ray powder diffraction. The diagram obtained is shown in FIG. 2.

Table 2 which follows summarises the data obtained in this analysis:

TABLE 2

X-ray powder reflections and intensities (standardised) of (R)-2-(4-amidinophenylaminomethyl)-1-methyl-5-[1-(carboxymethylamino)-1-(pyrrolidinocarbonyl)-ethyl]-benzimidazole.

| 2 Θ [°] | $d_{hkl}$ [Å] | intensity $I/I_o$ [%] | 2 Θ [°] | $d_{hkl}$ [Å] | intensity $I/I_o$ [%] |
|---|---|---|---|---|---|
| 7.331 | 12.04817 | 11.9 | 21.500 | 4.12969 | 15.8 |
| 10.804 | 8.18223 | 7.5 | 22.240 | 3.99395 | 7.9 |
| 11.572 | 7.64093 | 12.3 | 23.308 | 3.81335 | 19.4 |
| 12.312 | 7.18300 | 4.2 | 23.738 | 3.74525 | 9.4 |
| 12.976 | 6.81712 | 7.6 | 24.308 | 3.65862 | 8.2 |
| 13.726 | 6.44632 | 5.9 | 24.890 | 3.57442 | 8.3 |
| 14.295 | 6.19076 | 17.9 | 25.131 | 3.54076 | 7.9 |
| 14.726 | 6.01067 | 100.0 | 26.503 | 3.36044 | 4.7 |
| 15.365 | 5.76201 | 6.7 | 27.204 | 3.27547 | 7.3 |
| 17.168 | 5.16080 | 29.4 | 27.786 | 3.20815 | 9.6 |
| 18.014 | 4.92041 | 11.3 | 28.530 | 3.12608 | 7.5 |
| 18.309 | 4.84161 | 9.2 | 29.678 | 3.00774 | 6.3 |
| 19.168 | 4.62671 | 7.1 | 30.962 | 2.88589 | 5.0 |
| 20.224 | 4.38744 | 8.8 | 32.412 | 2.76004 | 4.3 |

In Table 1 above the value "2Θ[°]" denotes the angle of diffraction in degrees and the value "$d_{hkl}$ [Å]" denotes the specified distances in Å between the lattice planes.

The x-ray powder diagram was recorded, within the scope of the present invention, using a Bruker D8 Advanced-diffractometer fitted with a location-sensitive detector (OED) and a Cu anode as the x-ray source (CuK$_\alpha$ radiation, λ=1.5418 Å, 30 kV, 40 mA).

According to the findings shown in Table 2 the present invention relates to crystalline (R)-2-(4-amidinophenylaminomethyl)-1-methyl-5-[1-(carboxymethylamino)-1-(pyrrolidinocarbonyl)-ethyl]-benzimidazole, characterised in that in the x-ray powder diagram it has, inter alia, the characteristic values d=6.19 Å, 6.01 Å, 5.16 Å, 4.13 Å and 3.81 Å.

The invention further relates to the use of the crystalline base (R)-2-(4-amidinophenylaminomethyl)-1-methyl-5-[1-(carboxymethylamino)-1-(pyrrolidinocarbonyl)-ethyl]-benzimidazole according to the invention as a pharmaceutical composition on account of its pharmaceutical activity.

Solid Stress Stability Data of the Free Base and of the Corresponding Monohydrochloride

| Stress Parameters | Storage method | Stress conditions | Storage time | monohydrochloride | Free base |
|---|---|---|---|---|---|
| temperature | open glass dish | 105° C. | 24 hours | no decomposition | approx. 1 % decomposition |
| temperature and relative humidity | open glass dish | 70° C.; approx. 90% relative humidity | 3 days | no decomposition | approx. 4 % decomposition |
| light | open glass dish | Suntester xenon lamp | 22–24 hours | no significant decomposition (<1%) | approx. 1 % decomposition |

Experimental Section

The HPLC data given below were measured under the following parameters, unless otherwise stated:
Column: Prontosil 120-5-C18AQ, 5 μm, 125×4 mm; solvent A: 0.2% aqueous $KH_2PO_4$ solution, adjusted to pH=5.5 with 1 M NaOH; solvent B: acetonitrile; column temperature: 45° C.; flow: 1 mL/min; gradient system: up to 2 min 10% solvent B; within 14 min gradient to 60% solvent B, within 4 min gradient to 80% solvent B; concentration of the sample solution: 2 mg/mL in acetonitrile/water=7:3; injection volume: 1 μL; detection at 220 nm.

EXAMPLE 1

(R)-2-(4-amidinophenylaminomethyl)-1-methyl-5-[1-(n-propyloxycarbonylmethylamino)-1-(pyrrolidinocarbonyl)-ethyl]-benzimidazole-p-toluenesulphonic acid salt 442 g (2.09 mol) of n-propyl bromoacetate are poured into a solution of 700 g (1.74 mol) of (R)-2-(4-cyanophenylaminomethyl)-1-methyl-5-[1-amino-1-(pyrrolidinocarbonyl)-ethyl]-benzimidazole and 700 mL of diisopropylethylamine in 1.4 L of N-methylpyrrolidinone and 1.4 L of n-propylacetate within 15 minutes at 20° C. The reaction mixture is stirred for 14 hours at 20° C. 2.1 L of n-propylacetate and 5.6 L of water are added. The mixture is cooled to 20° C. and the aqueous phase is separated off. 3.5 L of water are added to the organic phase and this is adjusted to a pH of pH=5.8 by the addition of 30% hydrochloric acid. The aqueous phase is separated off. 3.5 L of water and 105 g of sodium chloride are added to the organic phase with stirring. The aqueous phase is separated off. The organic phase is concentrated by evaporation under reduced pressure using the rotary evaporator. 0.9 L of n-propylacetate and 3.5 L of n-propanol are added to the resulting oil. Another 3 litres of solvent are distilled off under reduced pressure.

3.5 L n-propanol are added to the residue and cooled to −15° C. 1.92 kg of hydrogen chloride gas are piped through this solution so that the temperature does not exceed 8° C. After the introduction of gas has ended the reaction mixture is stirred for 20 hours at 20° C. Then the reaction solution is cooled to 10° C. The reaction solution is stirred into a solution of 4.53 L of a 25% aqueous ammonia solution in 7 L of n-propanol cooled to −20° C., while the temperature is kept below 20° C. The reaction mixture is stirred for 16 hours at 24° C. 5.8 L of solvent are distilled off under reduced pressure. The reaction mixture is cooled to 45° C. and filtered through a pressure filter. The pressure filter is washed with 3.5 L of hot n-propanol. 8.8 L of solvent are distilled off from the filtrate in a rotary evaporator under reduced pressure. The residue remaining is suspended with 7 L acetone while heating and refluxing. The suspension is cooled to 0° C. and stirred for one hour at this temperature. The suspension is suction filtered and washed with 2.8 L acetone. The filter cake is dried at 50° C. in the circulating air drier. 1.23 kg of (R)-2-(4-amidinophenylaminome )-1-methyl-5-[1-(n-propyloxycarbonylmethylamino)-1-(pyrrolidinocarbonyl)-ethyl]-benzimidazole-hydrochloride are obtained

| HPLC: | $R_f$ = 9.9 min (product) |
|---|---|
| | $R_f$ = 12.9 min (bisalkylated by-product) |

Precipitation as p-toluenesulphonic Acid Salt:

1.22 kg of the crude hydrochloride described above are dissolved with stirring in 1.05 L n-propanol and 5.6 L water by heating to 55° C. To this solution is added a solution of 530 g of p-toluenesulphonic acid monohydrate and 146 mL of a 50% sodium hydroxide solution in 4.2 L of water. The resulting mixture is cooled to 0° C. and stirred for 30 minutes at this temperature. The suspension is suction filtered and washed with 3.5 L of water. The filter cake is dried in the circulating air drier at 50° C. 0.70 kg of the p-toluenesulphonic acid salt of the title compound are obtained as a crude product.

| HPLC: | $R_f$ = 3.6 min (p-toluenesulphonic acid) |
|---|---|
| | $R_f$ = 9.9 min (product) |
| | $R_f$ = 12.9 min (bisalkylated by-product) |

A further 0.19 kg of product are isolated from the mother liquor by adjusting the pH to pH=7.5 with 25% ammonia solution.

| Total yield: | 0.89 kg (73% of theory) |
|---|---|

Further Purification of the p-toluenesulphonic Acid Salt:

1.1 kg of the crude product of the p-toluenesulphonic acid salt described above are suspended in 13.2 L water at 20° C. 151 g of p-toluenesulphonic acid and 328 mL of 30% hydrochloric acid are added, whereupon the solid goes into solution and a pH of 1 to 1.5 is obtained. The pH is adjusted to 4 by the addition of 25% ammonia solution (approx. 170 mL). The resulting suspension is stirred for 19 hours at 20° C. The precipitate (bisalkylated by-product) is filtered off. The filter cake is washed with 2.2 L water. 1.54 L of n-propanol are added to the filtrate followed by 130 mL of 25% ammonia solution. The suspension is stirred overnight at 20° C. The precipitate is suction filtered and washed with 3.3 L water. The filter cake is dried at 50° C. in the circulating air drier. 0.83 kg (76% of theory) of the title compound are obtained.

| HPLC: | $R_f$ = 3.6 min (p-toluenesulphonic acid) |
|---|---|
| | $R_f$ = 9.9 min (product) |

EXAMPLE 2

Method of Preparing the Free Base by Ester Cleaving with Sodium Hydroxide Starting from the p-toluenesulphonic Acid Salt of the n-propyl Ester (R)-2-(4-amidinophenylaminomethyl)-1-methyl-5-[1-(carboxymethylamino)-1-(pyrrolidinocarbonyl)-ethyl]-benzimidazole To a solution of 27.7 g (40 mmol) of (R)-2-(4-amidinophenylaminomethyl)-1-methyl-5-[1-(n-propyloxycarbonymethylamino)-1-(pyrrolidinocarbonyl)-ethyl]-benzimidazole-p-toluenesulphonate in 134 mL of methanol are added 3.36 g (84 mmol) of solid sodium hydroxide and the mixture is refluxed for 3 hours. 8.37 g (44 mmol) of p-toluenesulphonic acid hydrate are added and the mixture is refluxed for a further 1.5 hours. The solution is allowed to cool to 40° C. and filtered (clear filtration). 170 mL methanol are added to the filtrate and it is inoculated. The suspension formed is stirred overnight at 20° C. The suspension is suction filtered and the filter cake is washed with 60 mL methanol. The product is dried in the circulating air drier at 40° C. The title compound is obtained as a crystalline solid.

| Yield: | 13.8 g (72% of theory) |
|---|---|
| melting point: | $T_{m.p.}$ = 249° C. ± 5° C. (decomposition, DSC, evaluating using onset, heating rate: 10° C./min) |

EXAMPLE 3

Method of Preparing the Free Base by Ester Cleaving with Sodium Hydroxide Starting from the Hydrochloride Salt of the n-propyl Ester (R)-2-(4-amidinophenylaminomethyl)-1-methyl-5-[1-(carboxymethylamino)-1-(pyrrolidinocarbonyl)-ethyl]-benzimidazole To a solution of 93.9 g (0.15 mol) of (R)-2-(4-amidinophenylaminomethyl)-1-methyl-5-[1-(n-propyloxycarbonylmethylamino)-1-(pyrrolidinocarbonyl)-ethyl]-benzimidazole-hydrochloride ×1 equivalent n-propanol in 470 mL methanol are added 13.3 g (0.33 mol) of solid sodium hydroxide and this mixture is refluxed for 1.5 hours under an inert gas atmosphere. It is allowed to cool to 50° C. and within 10 minutes 22.8 mL (0.18 mmol) of chlorotrimethylsilan are added dropwise thereto. The mixture is diluted with 470 mL of dimethylsulphoxide and 370 mL of methanol are distilled off at 300 mbar/80° C. To eliminate sodium chloride the suspension is filtered hot. The filtrate is cooled to 20° C. and stirred for 3 hours at 20° C. The suspension formed is suction filtered and the filter cake is washed with 50 mL dimethylsulphoxide and 100 mL acetone. The filter cake is dried at 50° C. in the circulating air drier. The title compound is obtained as a colourless solid.

| Yield: | 58.8 g (81% of theory) |
|---|---|

For further purification the product thus obtained may be crystallised from methanol.

| melting point: | $T_{m.p.}$ = 241° C. ± 5° C. (decomposition, DSC, evaluated via onset, heating rate: 10° C./min) |
|---|---|

EXAMPLE 4

Method of Precipitating the Monohydrochloride from the Free Base (R)-2-(4-amidinophenylaminomethyl)-1-methyl-5-[1-(carboxymethylamino)-1-(pyrrolidinocarbonyl)-ethyl]-benzimidazole-monohydrochloride A suspension of 11 g (23 mmol) of (R)-2-(4-amidinophenylaminomethyl)-1-methyl-5-[1-(carboxymethylamino)-1-(pyrrolidinocarbonyl)-ethyl]-benzimidazole in 88 mL methanol is heated to 35° C. to 40° C. To this suspension are added 8.4 mL of a 2.75 molar solution of hydrogen chloride (23 mmol) in ethyl acetate. The starting material is dissolved and the hydrochloride begins to crystallise out. The suspension is cooled to 20° C. and suction filtered. The filter cake is dried in the vacuum drying cupboard at 35° C. 9.2 g (78% of theory) of the title compound are obtained as a crystalline solid. To eliminate traces of methanol 8 g of the title compound obtained above are suspended in 80 mL of ethanol and stirred for 30 minutes at 50° C. The suspension is cooled to 20° C. and suction filtered. The filter cake is washed with ethanol and dried in the vacuum drying cupboard at 35° C.

| Yield: | 7.3 g (91% of theory based on hydrochloride used) |
|---|---|
| melting point: | $T_{m.p.}$ = 222° C. ± 5° C. (decomposition, DSC, evaluated via onset, heating rate: 10° C./min) |

EXAMPLE 5

(R)-2-(4-Amidinophenylaminomethyl)-1-methyl-5-[1-(ethyloxycarbonylmethylamino)-1-(pyrrolidinocarbonyl )-ethyl]-benzimidazole-p-toluenesulphonic acid salt 4.22 kg (10.5 mol) of (R)-2-(4-cyanophenylaminomethyl)-1-methyl-5-[1-amino-1-(pyrrolidinocarbonyl)-ethyl]-benzimidazole and 3.11 kg (24.1 mol) of diisopropylethylamine are dissolved in a mixture of 8.4 L of N-methylpyrrolidinone and 8.4 L of ethylacetate. 2.1 kg (12.6 mol) of ethyl bromoacetate are metered in and the mixture is stirred for 15 hours at 20° C. 34 L of water are added. The aqueous phase is separated off. 21 L of water are added to the organic phase and the pH is adjusted to 5.7 by the addition of hydrochloric acid (30%). The aqueous phase is separated off and the organic phase is washed with a solution of 0.42 kg of sodium chloride in 21 L of water. The organic phase is concentrated under reduced pressure (10.6 L of ethyl acetate are distilled off). The concentrate is diluted with 42 L of ethanol and concentrated again under reduced pressure (21 L are distilled off). At 20° C. 15 kg (411 mol) of hydrochloric acid gas are piped into the resulting solution and it is stirred at 20° C. until the reaction is complete (the reaction to obtain the iminoester is monitored by HPLC). The iminoester solution formed is diluted with 25 L of ethanol. 37.8 kg (555 mol) of ammonia solution (25%) are added to the solution so that the temperature does not exceed 40° C. The solution is then stirred for 2 hours. The ammonium chloride formed is filtered through a pressure filter and the filtered material is washed with 30 L of ethanol. 42 L of ethanol are distilled off from the filtrate under reduced pressure. A solution of 3.86 kg (20.3 mol) of p-toluenesulphonic acid monohydrate in 17 L of water is added to the filtrate. Another 20 L of water are added. The pH is adjusted to 8.0 with sodium hydroxide solution (50%). The remaining ethanol is distilled off under reduced pressure. Towards the end of the distillation the product crystallises out. The pH is adjusted to 7.5 with sodium hydroxide solution (50%) and the suspension formed is cooled to 3° C. The product is centrifuged off and washed with 13 L of water. The product is dried in the drying cupboard at 50° C. 4.89 kg (69% of theory) of the title compound are obtained in the form of the crude product.

Further Purification of the p-toluenesulphonic Acid Salt:

4.75 kg of the crude product are suspended in 38 L of water. The suspension is stirred for 2.5 hours at 20° C. The suspension is centrifuged off and washed with 19 L of water. The product is dried at 50° C. in the drying cupboard. 3.86 kg (81% of theory) of the title compound are obtained.

| HPLC: | $R_f$ = 3.6 min (p-toluenesulphonic acid) |
| --- | --- |
|  | $R_f$ = 17.6 min (product) |

Column: Inertsil ODS-2, 5 μm, 125×4.6 mm; solvent A: 0.3% aqueous $KH_2PO_4$ solution, adjusted to pH=5.0 with 1 M NaOH; solvent B: acetonitrile; column temperature: 45° C.; flow: 1 mL/min; gradient system: start: 10% solvent B; within 20 min gradient to 25% solvent B, within 10 min gradient to 50% solvent B; concentration of the sample solution: 2 mg/mL in acetonitrile/water=7:3; injection volume: 3 μL; detection at 217 nm.

EXAMPLE 6

Method of Preparing the Free Base by Ester Cleaving with Potassium Hydroxide Starting from the p-toluenesulphonic Acid Salt of the Ethyl Ester (R)-2-(4-Amidinophenylaminomethyl)-1-methyl-5-[1-(carboxymethylamino)-1-(pyrrolidinocarbonyl)-ethyl]-benzimidazole 3.7 kg (5.49 mol) of (R)-2-(4-amidinophenylaminomethyl)-1-methyl-5-[1-(ethyloxycarbonylmethylamino)-1-(pyrrolidinocarbonyl)-ethyl]-benzimidazol-p-toluenesulphonic acid salt are dissolved in 7.4 L of methanol at 40° C. To this solution is added a solution of 0.795 kg (12.8 mol) of potassium hydroxide powder in 5.6 L of methanol und this is then rinsed with 1.8 L of methanol. The mixture is stirred for 2.5 hours at 40° C. The potassium salt of the p-toluenesulphonic acid crystallises out. A solution of 1.37 kg (7.2 mol) of p-toluenesulphonic acid monohydrate in 2.8 L of methanol is added to the suspension, this is rinsed with 1.8 litres of methanol and cooled to 22° C. The precipitated potassium salt of p-toluenesulphonic acid is separated off using a pressure filter and the filter cake is washed with 7.4 litres of methanol. The filtrate is inoculated with the title compound and stirred overnight. The precipitated product is suction filtered under argon, washed with 3.7 L of methanol and recycled into the reactor while still damp. 18.5 L of methanol are added and the suspension is refluxed for one hour and cooled to 22° C. The product is suction filtered under argon, washed with 3.7 L of methanol and dried at 30° C. in a circulating air drier. 2.22 kg (85% of theory) of the title compound are obtained.

| Melting point: | $T_{m.p.}$ = 241° C. ± 5° C. (decomposition, DSC, evaluated using onset, heating rate: 10° C./min, measured with DSC 204 of Messrs Netzsch-Gerätebau GmbH) |
| --- | --- |

EXAMPLE 7

Method of Precipitating the Monohydrochloride from Ethanol (R)-2-(4-Amidinophenylaminomethyl)-1-methyl-5-[1-(carboxymethylamino)-1-(pyrrolidinocarbonyl)-ethyl]-benzimidazole-monohydrochloride 5.0 g of (R)-2-(4-amidinophenylaminomethyl)-1-methyl-5-[1-(carboxymethylamino)-1-(pyrrolidinocarbonyl)-ethyl]-benzimidazole are refluxed in 25 mL of ethanol. After the addition of 2 mL of water a solution is obtained. The solution is filtered clear and the filter is rinsed with 25 mL of ethanol. The filtrate is heated to 70° C. A solution of 0.802 mL of conc. hydrochloric acid in 25 mL of ethanol is added and then another 25 mL of ethanol are added. The mixture is cooled to 25° C. and stirred for one hour at this temperature. The product is filtered off, washed with 15 mL of ethanol and dried in the circulating air drier.

4.95 g (92% of theory) of the title compound are obtained as a crystalline solid

| Melting point: | $T_{m.p.}$ = 220° C. ± 5° C. (decomposition, DSC, evaluating using onset, heating rate: 10° C./min) |
| --- | --- |

BRIEF DESCRIPTION OF THE FIGURES

FIG. 1 shows the x-ray powder diffractogram of the crystalline monohydrochloride of the compound (R)-2-(4-amidinophenylaminomethyl)-1-methyl-5-[1-(carboxymethylamino)-1-(pyrrolidinocarbonyl)-ethyl]-benzimidazole.

FIG. 2 shows the x-ray powder diffractogram of the crystalline compound (R)-2-(4-amidinophenylaminomethyl)-1-methyl-5-[1-(carboxymethylamino)-1-(pyrrolidinocarbonyl)-ethyl]-benzimidazole.

What is claimed is:

1. Crystalline (R)-2-(4-amidinophenylaminomethyl)-1-methyl-5-[1-(carboxymethylamino)-1-(pyrrolidinocarbonyl)-ethyl]-benzimidazole-monohydrochloride, wherein the x-ray powder diagram thereof has inter alia the characteristic values d=8.66 Å, 7.84 Å, 6.31 Å, 6.07 Å, 5.67 Å, 5.14 Å, 4.18 Å, 3.72 Å, 3.67 Å and 3.51 Å; and having a melting point of $T_{m.p.}=222\pm5°$ C.

2. Crystalline (R)-2-(4-amidinophenylaminomethyl)-1-methyl-5-[1-(carboxymethylamino)-1-(pyrrolidinocarbonyl)-ethyl]-benzimidazole, the x-ray powder diagram of which has inter alia the characteristic values d=12.05 Å, 7.64 Å, 6.19 Å, 6.01 Å, 5.16 Å, 4.84 Å, 4.92 Å, 4.13 Å, 3.81 Å, 3.75 Å and 3.21 Å; and having a melting point of $T_{m.}=241\pm5°$ C.

* * * * *